US007314742B2

(12) United States Patent
MacPhee et al.

(10) Patent No.: US 7,314,742 B2
(45) Date of Patent: *Jan. 1, 2008

(54) LIPOPROTEIN ASSOCIATED PHOSPHOLIPASE A2, INHIBITORS THEREOF AND USE OF THE SAME IN DIAGNOSIS AND THERAPY

(75) Inventors: Colin Houston MacPhee, Letchworth (GB); David Graham Tew, Groby (GB); Christopher Donald Southan, London (GB); Deirdre Mary Bernadette Hickey, Saffron Walden (GB); Israel Simon Gloger, London (GB); Geoffrey Mark Prouse Lawrence, Sawbridgeworth (GB); Simon Quentyn John Rice, Buntingford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/108,519

(22) Filed: Apr. 18, 2005

(65) Prior Publication Data

US 2005/0260731 A1    Nov. 24, 2005

Related U.S. Application Data

(63) Continuation of application No. 09/922,067, filed on Aug. 3, 2001, now Pat. No. 7,045,329, which is a continuation of application No. 09/193,130, filed on Nov. 17, 1998, now abandoned, which is a continuation of application No. 08/387,858, filed as application No. PCT/GB94/01374 on Jun. 24, 1994, now Pat. No. 5,981,252.

(30) Foreign Application Priority Data

Jun. 25, 1993 (GB) ................. 9313144.9
Jan. 11, 1994 (GB) ................. 9400413.2

(51) Int. Cl.
*C12N 9/00* (2006.01)
*C12N 9/20* (2006.01)

(52) U.S. Cl. .............. 435/198; 435/4; 435/6; 435/69.1; 435/183; 435/192; 435/252.3; 435/320.1; 536/23.2; 536/23.5

(58) Field of Classification Search ............... 435/4, 435/6, 69.1, 183, 198, 200, 252.3, 320.1; 536/23.2; 530/350

See application file for complete search history.

(56) References Cited

U.S. PATENT DOCUMENTS

| 5,527,698 A | 6/1996 | Knopf et al. |
| 5,532,152 A | 7/1996 | Cousens et al. |
| 5,641,669 A | 6/1997 | Cousens et al. |
| 5,840,839 A | 11/1998 | Wang et al. |
| 5,968,818 A | 10/1999 | Gloger et al. |
| 5,981,252 A * | 11/1999 | MacPhee et al. ........... 435/198 |

FOREIGN PATENT DOCUMENTS

| EP | 0359425 A1 | 8/1988 |
| EP | 0509719 A1 | 10/1992 |
| WO | WO89/09818 | 10/1989 |
| WO | WO95/00649 | 1/1995 |

OTHER PUBLICATIONS

Steinbrecher et al. J. Lipid Res., 1989, vol. 30(3) :305-315.*
Stremler KE et al. J. Biol. Chem., 1989, vol. 264(10):5331-5334.*
U.S. Appl. No. 10/415,682, filed May 2003, Campbell, et al.
U.S. Appl. No. 11/141,554, filed May 2005, MacPhee, et al.
Chandrakumar NS, et al., "Stereospecific Synthesis of Ether Phospholipids. Preparation of a-Alkyl-2-(acylamino)-2-deoxyglycerophosphoryl cholines," *J. Org. Chem.*, 1197-1202 (1983).
Ponpipom MM, et al., "Synthesis of Azide and Amide Analogs of Platelet-Activating Factors and Related Derivatives," *Chem. Phys. Lipids.* 35:29-37 (1984).
Stafforini D, et al., "Human plasma platelet-activating factor acetylhydrolase," *J. Biol. Chem.* 262(9):4223-4230 (1987).
Stafforini D, et al. "Human macrophages secrete plate-activating factor acetylhydrolase," *J. Biol. Chem.* 265(17):9682-9687 (1990).
Langlais J., et al., Platelet-activating factor acetyl-hydrolase in human semen: a novel decapacitation factor? *Biol. of Reprod.* 44 (Suppl.1):94 (1991).
Hong S. et al. "Safety and Short Term Toxicity of a Novel Cationic Lipid Formulation for Human Gene Therapy," *Human Gene Therapy:* 781-798 (1993).
Kim UT, et al. "Synthesis of Phospholipid Headgroups via Nucleophilic Ring Opening of 1.3.2-Dioxaphospholanes," *J. Chem. Soc. Chem. Commun.:* 70-71 (1993).
Christofferson R, et al. "Ribozymes as Human Therapeutic Agents," *J. of Medicinal Chem.:* 2023-2037 (1994).
Stull R, et al., "Antigene, Ribozyme, and Aptomer Nucleic Acid Drugs: Progress and Prospects," *Pharm. Res.* 12(4):465-483(1995).
Steinbrecher et al., "Hydrolysis of phosphatidylcholine during LDL oxidation is mediated by platelet-activating factor acetylhydrolase," *J. Lipid Res.*, 30(3) :305-315 (1989).

(Continued)

*Primary Examiner*—Manjunath Rao
(74) *Attorney, Agent, or Firm*—Andrea V. Lockenour; Edward R. Gimmi (57) ABSTRACT

The enzyme Lp-PLA$_2$ in purified form, an isolated nucleic acid molecule encoding Lp-PLA$_2$, the use of an inhibitor of the enzyme Lp-PLA$_2$ in therapy and a method of screening compounds to identify those compounds which inhibit the enzyme.

2 Claims, 2 Drawing Sheets

OTHER PUBLICATIONS

Stremier K E, et al., "An Oxidized Derivative of Phosphatidylcholine is a Substrate for the Platelet-activating Factor Aceylhydrolase from Human Plasma," *J. Biol. Chem.*, 264(10):5331-5334 (1989).

Sevier ED, et al., "Monoclonal Antibodies in Clinical Immunology," *Clinical Chem.* 27:1797-1806 (1981).

Kohler G, et al., "Continuous Cultures of Fused Cells Secreting Antibody of Predefined Specificity" *Nature* 236:495-497 (Aug. 7, 1975).

Bell, Rachel, et al., "Systematic screening of the LDL-PLA2 gene for polymorphic variants and case-control polymorphic variants and case-control analysis in schizophrenia," *Biochemical and Biophysical Research Communications*, 241(3): 630-635 (1997) XP002197530.

Yamada, Yoshiji, et al., "Correlations between plasma platelet-activating factor acetylhydrolase (PAF-AH) activity and PAF-AH genotype, age, and atherosclerosis in a Japanese Population", *Atherosclerosis*, 150(1):209-216(2000) XP002197527.

Hiramoto, Maoto, et al., "A mutation in plasma platelet-activating factor acetylhydrolase (Val279fwdarwPhe) is a genetic risk factor for stroke." *Stroke*, 28(12):2417-2420 (Dec. 12, 1997) XP002197528.

Kruse, Susanne, et al., "The Ile198Thr and Ala379Val variants of plasmatic Paf-acetylhydrolase impair catalytical activites and are associated with atopy and asthma," *Am. Journal of Human Genetics*, 66(5):1522-1530 (2000) XP002197529.

Tew, D. G., et al., "Purification, properties, sequencing and cloning of a lipo-protein-associated, serine-dependent phospholipase involved in the oxidative modification of low-density lipoproteins", *Arteriosclerosis Thrombosis and Vascular Biology*, 16(4):591-599 (Apr. 1996).

Tjoelker, I. W., "Anti-inflammatory properties of a platelet-activating factor acetylhydrolase", *Nature, MacMillan Journals Ltd., London*, 374(6):549-553 (Apr. 1995) XP002109103.

Langlais J. et al., Platelet-activating factor acetyl-hydrolase in human semen: a novel decapacitation factor? Biol. of Reprod. 44 (Suppl. 1):94 (1991).

San H, et al. "Safety and Short Term Toxicity of a Novel and Cationic Formulation for Human Gene Therapy," Human Gene Therapy: 781-798 (1993)

\* cited by examiner

FIGURE 1

Fig.1 Compound 4 inhibits copper (5μM) - stimulated LDL (150μg/ml) oxidation.

FIGURE 2

Lanes 2, 4 and 6 contain adjacent fractions of purified native Lp-PLA2. Lanes 1, 3 and 5 are fractions 2, 4 and 6 respectively after N-deglycosylation.

LIPOPROTEIN ASSOCIATED PHOSPHOLIPASE A2, INHIBITORS THEREOF AND USE OF THE SAME IN DIAGNOSIS AND THERAPY

This is a Continuation of application 09/922,067, filed Aug. 3, 2001, now U.S. Pat. No. 7,045,329, which is a Continuation of Ser. No. 09/193,130 filed Nov. 17, 1998, now abandoned, which is a Continuation Ser. No. 08/387,858, filed Feb. 24, 1995, now U.S. Pat. No. 5,981,252, which is a §371 of International Application No. PCT/GB94/01374 filed Jun. 24, 1994, which claims priority of Great Britain Application Nos. GB 9313144.9 filed Jun. 25, 1993, and 9400413.2, filed Jan. 11, 1994.

The present invention relates to the use of inhibitors of an enzyme in the therapy, in particular in the treatment of atherosclerosis. The present invention also relates to the isolation and purification of the enzyme, to isolated nucleic acids encoding the enzyme, to recombinant host cells transformed with DNA encoding the enzyme, to the use of the enzyme in diagnosing a patient's susceptibility to atherosclerosis, and to the use of the enzyme in identifying compounds which are potentially useful for the treatment of atherosclerosis.

Lipoprotein Associated Phospholipase $A_2$ (Lp-PLA$_2$), also previously known in the art as Platelet Activating Factor Acetyl Hydrolase (PAF acetyl hydrolase). During the conversion of LDL to its oxidised form, Lp-PLA$_2$ is responsible for hydrolysing the sn-2 ester of oxidatively modified phosphatidylcholine to give lyso-phosphatidylcholine and an oxidatively modified fatty acid. Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis. Inhibition of the Lp-PLA$_2$ enzyme would therefore be expected to stop the build up of this fatty streak (by inhibition of the formation of lysophosphatidylcholine), and so be useful in the treatment of atherosclerosis. In addition, it is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process. In keeping with this idea, Lp-PLA$_2$ inhibitors inhibit LDL oxidation. Lp-PLA$_2$ inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction, reperfusion injury and acute and chronic inflammation.

The present invention therefore provides in a first aspect an inhibitor of the enzyme lipoprotein associated Lp-PLA$_2$ for use in therapy, in particular in the treatment of atherosclerosis. Suitable compounds able to inhibit the Lp-PLA$_2$ enzyme are known in the art and include for example, the following compounds of structure (I):

in which R is $C_{1-6}$alkylCONR$^2$;
 R$^2$ is hydrogen or $C_{1-6}$alkyl;
 X is oxygen, sulphur or —O(CO)—;
 R$^1$ is $C_{8-20}$alkyl;
 Z is N(R$^3$)$_2$, $^{\oplus}$N(R$^3$)$_3$, SR$^3$, $^{\oplus}$S(R$^3$)$_2$, in which each group R$^3$ is the same or different and is $C_{1-6}$ alkyl, OR$^2$, $C_{1-4}$alkanoyl, imidazolyl or N-methylimidazolyl Suitably R$^2$ is hydrogen or $C_{1-6}$ alkyl; preferably R$^2$ is hydrogen.

Suitably X is oxygen, sulphur or —O(CO)—; preferably X is oxygen

Suitably R$^1$ is $C_{8-20}$alkyl; preferably R$^1$ is $C_{16-18}$ alkyl

Suitably Z is N(R$^3$)$_2$, $^{\oplus}$N(R$^3$)$_3$, SR$^3$, $^{\oplus}$S(R$^3$)$_2$, in which each group R$^3$ is the same or different and is $C_{1-6}$ alkyl, OR$^2$, $C_{1-4}$alkanoyl, imidazolyl or N-methylimidazolyl; preferably Z is SR$^3$ in which R$^3$ is methyl or OR$^2$ in which R$^2$ is hydrogen The compounds of structure (I) can be prepared by processes known to those skilled in the art, for example as described in J Chem Soc Chem Comm, 1993, 70-72; J Org Chem, 1983, 48, 1197 and Chem Phys Lipids, 1984,35,29-37 or procedures analogous thereto.

When used in therapy, the compounds of structure (I) are formulated in accordance with standard pharmaceutical practice.

The compounds of structure (I) and their pharmaceutically acceptable salts which are active when given orally can be formulated as liquids, for example syrups, suspensions or emulsions, tablets, capsules and, lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (1) or a pharmaceutically acceptable salt thereof calculated as the free base, the compound being administered 1 to 4 times per day. Suitably the compounds will be administered for a period of continuous therapy.

The enzyme, lipoprotein associated Lp-PLA$_2$ has not hitherto been available in isolated purified form. The present invention therefore provides in a further aspect, the enzyme lipoprotein associated Lp-PLA$_2$ in purified form. By purified form is meant at least 80%, more preferably 90%, still more preferably 95% and most preferably 99% pure with respect to other protein contaminants.

The enzyme Lp-PLA$_2$ may be characterised by one or more partial peptide sequences selected from SEQ ID NOs: 1, 2, 3, 4, 10 and 11 or by the partial peptide sequence comprising residues 271 to 441 or consisting of residues 1 to 441 of SEQ ID NO:9. The enzyme Lp-PLA$_2$ may further or alternatively characterised by its molecular weight found to be 45 kDa, at least 45 kDa, 45-47 kDa, 4647 kDa or 45-50 kDa.

The invention also provides fragments of the enzyme having Lp-PLA$_2$ activity.

The enzyme can be isolated and purified using the methods hereafter described. Once isolated, the protein sequence of the enzyme can be obtained using standard techniques. In identifying said sequence, a number of protein fragments have been identified, each of which comprises part of the whole sequence of the enzyme. These sequences are themselves novel and form a further aspect of the invention.

This invention also provides isolated nucleic acid molecules encoding the enzyme, including mRNAs, DNAs, cDNAs as well as antisense analogs thereof and biologically active and diagnostically or therapeutically useful fragments thereof.

In particular, the invention provides an isolated nucleic acid molecule consisting of bases 1 to 1361 or 38 to 1361 or comprising the sequence corresponding to bases 848 to 1361 of SEQ ID NO: 9.

This invention also provides recombinant vectors, such as cloning and expression plasmids useful as reagents in the recombinant production of the enzyme, as well as recombinant prokaryotic and/or eukaryotic host cells comprising the novel nucleic acid sequence.

This invention also provides nucleic acid probes comprising nucleic acid molecules of sufficient length to specifically hybridize to the novel nucleic acid sequences.

This invention also provides an antisense oligonucleotide having a sequence capable of binding with mRNAs encoding the enzyme so as to prevent the translation of said mRNA.

This invention also provides transgenic non-human animals comprising a nucleic acid molecule encoding the enzyme. Also provided are methods for use of said transgenic animals as models for mutation and SAR (structure/activity relationship) evaluation as well as in drug screens.

This invention further provides a method of screening compounds to identify those compounds which inhibit the enzyme comprising contacting isolated enzyme with a test compound and measuring the rate of turnover of an enzyme substrate as compared with the rate of turnover in the absence of test compound.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the sense strand of DNA.

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule and includes allelic variations. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g. "Current Protocols in Mol. Biol." Vol. I & II, Wiley Interscience. Ausbel et al. (ed.) (1992). Protein sequences that are substantially the same can be identified by proteolytic digestion, gel electrophoresis and microsequencing.

The term "functionally equivalent" intends that the amino acid sequence of the subject protein is one that will exhibit enzymatic activity of the same kind as that of Lp-PLA$_2$.

A "heterologous" region of a DNA construct is an identifiable segment of DNA within or attached to another DNA molecule that is not found in association with the other molecule in nature.

This invention provides an isolated nucleic acid molecule encoding the enzyme Lp-PLA$_2$. One means for isolating the coding nucleic acid is to probe a human genomic or cDNA library with a natural or artificially designed probe using art recognized procedures (See for example: "Current Protocols in Molecular Biology", Ausubel, F. M, et al. (eds.) Greene Publishing Assoc. and John Wiley Interscience, New York, 1989, 1992); for example using the protein fragment information disclosed herein. The enzyme of this invention may be made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g. yeast, insect or mammalian) cells by methods well known in the art (Ausubel et al., supra). The coding sequences for the desired proteins having been prepared or isolated, can be cloned into a suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), a baculovirus insect cell system, YCp19 (*Saccharomyces*). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The protein sequences of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site. Modification of the coding sequences may also be performed to alter codon usage to suit the chosen host cell, for enhanced expression.

In some cases, it may be desirable to add sequences which cause the secretion of the polypeptide from the host organism, with subsequent cleavage of the secretory signal. It may also be desirable to produce mutants or analogs of the enzyme of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the ar See, e.g., T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437;

4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327-341) which uses the SV40 late promoter to drive expression in mammalian cells or pCDNA1neo, a vector derived from pCDNA1 (*Mol. Cell Biol.* 7:4125-29) which uses the CMV promoter to drive expression. Both these latter two vectors can be employed for transient or stable (using G418 resistance) expression in mammalian cells. Insect cell expression systems, e.g., *Drosophila*, are also useful, see for example, PCT applications U.S. 89/05155 and U.S. 91/06838 as well as EP application 88/304093.3.

Depending on the expression system and host selected, the enzyme of the present invention may be produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. Where the protein is localized to the cell surface, whole cells or isolated membranes can be used as an assayable source of the desired gene product. Protein expressed bacterial hosts such as *E. coli* may require isolation from inclusion bodies and refolding. The selection of the appropriate growth conditions and recovery methods are within the skill of the art.

The identification of this novel target for the treatment of atherosclerosis, also leads to a novel diagnostic method to diagnose a patient's susceptibility to developing atherosclerotic disease.

The present invention therefore provides in a still further aspect a diagnostic method comprising isolating a sample of blood from the patient, and assaying said sample for Lp-PLA$_2$ activity. Patients that are susceptible to atherosclerotic disease are expected to have elevated levels of the Lp-PLA$_2$ enzyme, and hence the levels of Lp-PLA$_2$ provides an indication of the patient's susceptibility to atherosclerotic disease. Moreover, Lp-PLA$_2$ is found located predominantly on dense subfraction(s) of LDL which are known to be very atherogenic. Plasma Lp-PLA$_2$ levels could therefore provide a ready measure of these very atherogenic small dense LDL particles.

It is expected that the presence of the enzyme in the blood sample of the patient can be assayed by analysis of enzyme activity (i.e. by an assay set up against the purified enzyme as standard); or alternatively by assaying protein content of the sample by using polyclonal or monoclonal antibodies prepared against the purified enzyme. Monoclonal (and polyclonal) antibodies raised against the purified enzyme or fragments thereof are themselves novel and form a further aspect of the invention.

Data and Examples

1. Screen for Lp-PLA$_2$ Inhibition.

Enzyme activity was determined by measuring the rate of turnover of the artificial substrate (A) at 37° C. in 50 mM HEPES (N-2-hydroxyethylpiperazine-N'-2-ethanesulphonic acid) buffer containing 150 mM NaCl, pH 7.4.

(A)

Assays were performed in 96 well titre plates.

Lp-PLA$_2$ was pre-incubated at 37° C. with vehicle or test compound for 10 min in a total volume of 180 μl. The reaction was then initiated by the addition of 20 μl 10× substrate (A) to give a final substrate concentration of 20 μM. The reaction was followed at 405 nm for 20 minutes using a plate reader with automatic mixing. The rate of reaction was measured as the rate of change of absorbance.

| Compound No | XR$^1$ | R | Z | IC$_{50}$(μM) |
|---|---|---|---|---|
| 1 | O(CH$_2$)$_{15}$CH$_3$ | CH$_3$CONH | N$^+$(CH$_3$)$_3$ | 0.8 |
| 2 | O(CH$_2$)$_{17}$CH$_3$ | CH$_3$CONH | N$^+$(CH$_3$)$_3$ | 3.5 |
| 3 | O(CH$_2$)$_{17}$CH$_3$ | CH$_3$CONH | S$^+$(CH$_3$)$_2$ | 1.0 |
| 4 | O(CH$_2$)$_{17}$CH$_3$ | CH$_3$CONH | SCH$_3$ | 0.08 |
| 5 | O(CH$_2$)$_{17}$CH$_3$ | CH$_3$CONH | OH | 0.45 |
| 6 | O(CH$_2$)$_{17}$CH$_3$ | CH$_3$CONH | OAc | 0.2 |
| 7 | O(CH$_2$)$_{17}$CH$_3$ | CH$_3$CONH | imidazole | 0.5 |
| 8 | O(CH$_2$)$_{17}$CH$_3$ | CH$_3$CONH | N-methylimidazolium | 0.55 |
| 9 | O(CH$_2$)$_{17}$CH$_3$ | CF$_3$CONH | N$^+$(CH$_3$)$_3$ | 2.5 |

Figure 1:
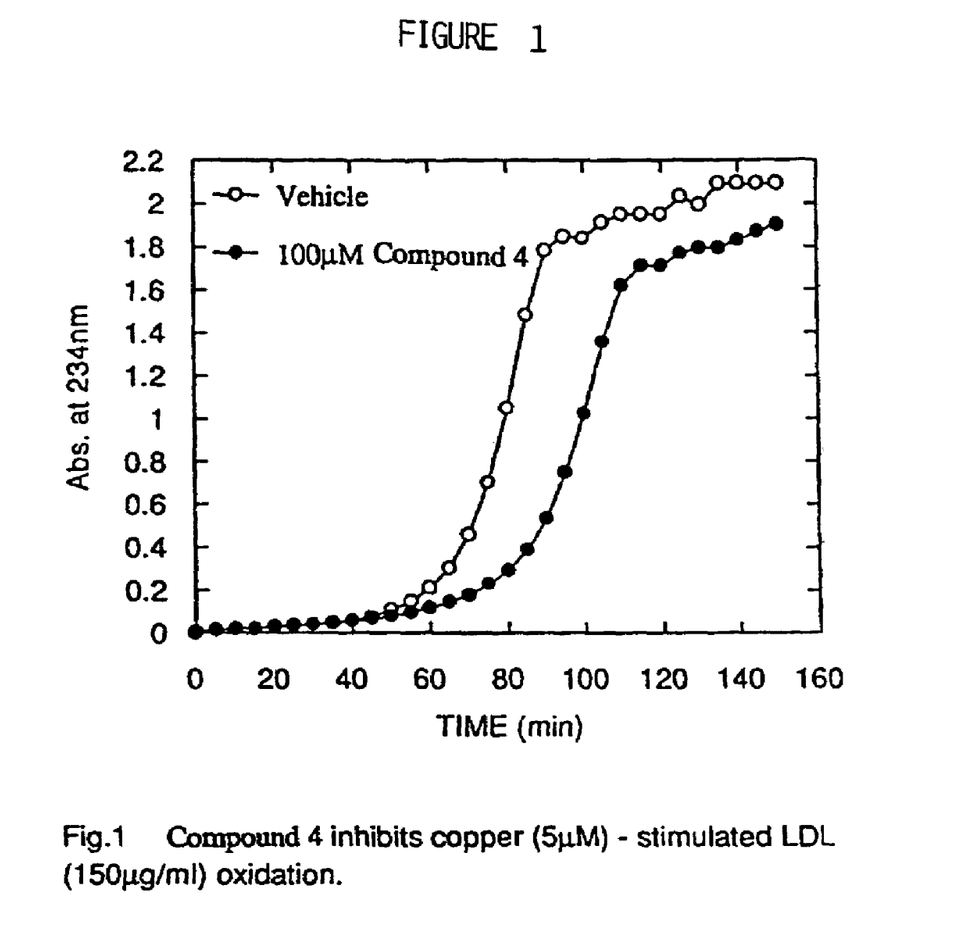
FIG. 1 is a graph of absorbance at 234 nm against time (min) in a study of inhibition of copper (5 µM)-stimulated LDL (150 µg/ml) oxidation by compound 4 vs control vehicle.

2. Copper Stimulated LDL Oxidation:

Copper stimulated oxidation of LDL is routinely measured by following the increase in conjugated diene formation by monitoring the change in absorption at 234 nm. This assay can be used to study inhibitors of oxidative modification of LDL FIG. 1 demonstrates that Lp-PLA$_2$ inhibitors are effective inhibitors of LDL oxidation through a prolongation of the lag phase, using compound 4 as an example.

3. Inhibition of Cu 2+Stimulated Lyso-Phosphatidylcholine (Lyso-PtdCho) Formation.

A 1 ml aliquot of human LDL (0.25 mg protein/ml) was incubated for 15 min at 37° C. with compound or vehicle. 5 μM Cu$^{2+}$ was then added to allow oxidation/lyso-PtdCho formation to occur. The incubation was terminated by the addition of 3.75 ml chloroform/methanol/c HCl (200:400:5, v/v/v). Following the addition of 1.25 ml chloroform and 1.25 ml 0.1M HCl, the mixture was vortexed and centrifuged. The lower phase was carefully removed and the upper phase re-extracted with an equal volume of synthetic lower phase. The extracts were pooled and dried under nitrogen.

Phospholipids were reconstituted into 50 μl chloroform/methanol (2:1 v/v). 10 μl aliquots were spotted on to pre-run silica gel HPTLC plates and then developed in chloroform/methanol 25-30% methylamine (60:20:5 v/v/v). Plates were subsequently sprayed with the flourescent indicator, 2-p-toluidinylnaphthalene-6-sulphonic acid (1 mM in 50 mM Tris/HCl, pH 7.4) to identify phospholipid components. Fluorescence was measured at 222 nm using a CAMAG TLC scanner. Lipoprotein lyso-PtdCho content was quantified using a standard curve (0.05-0.5 µg) prepared in parallel.

Compound 4 dose dependently inhibits LDL lyso-PtdCho accumulation stimulated by copper ions with an $IC_{50}$ value of ~30 µM.

4. Purification of Lipoprotein Associated Lp-PLA$_2$

Low density lipoprotein (LDL) was obtained by plasma apheresis. The LDL was dialysed against 0.5 M NaCl, 50 mM MES (4-morpholine ethane sulphonic acid), pH=6.0 overnight at 4° C. Solid CHAPS (3-[(−3-cholamidopropyl) dimethylamino]-1-propane sulphonate) was added to 10 mM and the LDL stirred for 30 minutes to effect solubilisation. The solubilised LDL was pumped onto a pre-equilibrated Blue Sepharose 6FF (Pharmacia) column (2.6×20 cm). The column was then washed with 50 mM MES, 10 mM CHAPS, 0.5 M NaCl, pH=6.0 followed by 50 mM Tris, 10 mM CHAPS, 0.5 M NaCl, pH=8.0 until the absorbance (280 nm) of the eluate reached zero. Lp-PLA$_2$ was eluted using 50 mM Tris, 10 mM CHAPS, 1.5 M NaCl, pH=8.0. The Lp-PLA$_2$ fraction was then concentrated and dialysed overnight against 50 mM Tris, 10 mM CHAPS, pH=8.0.

Figure 2:
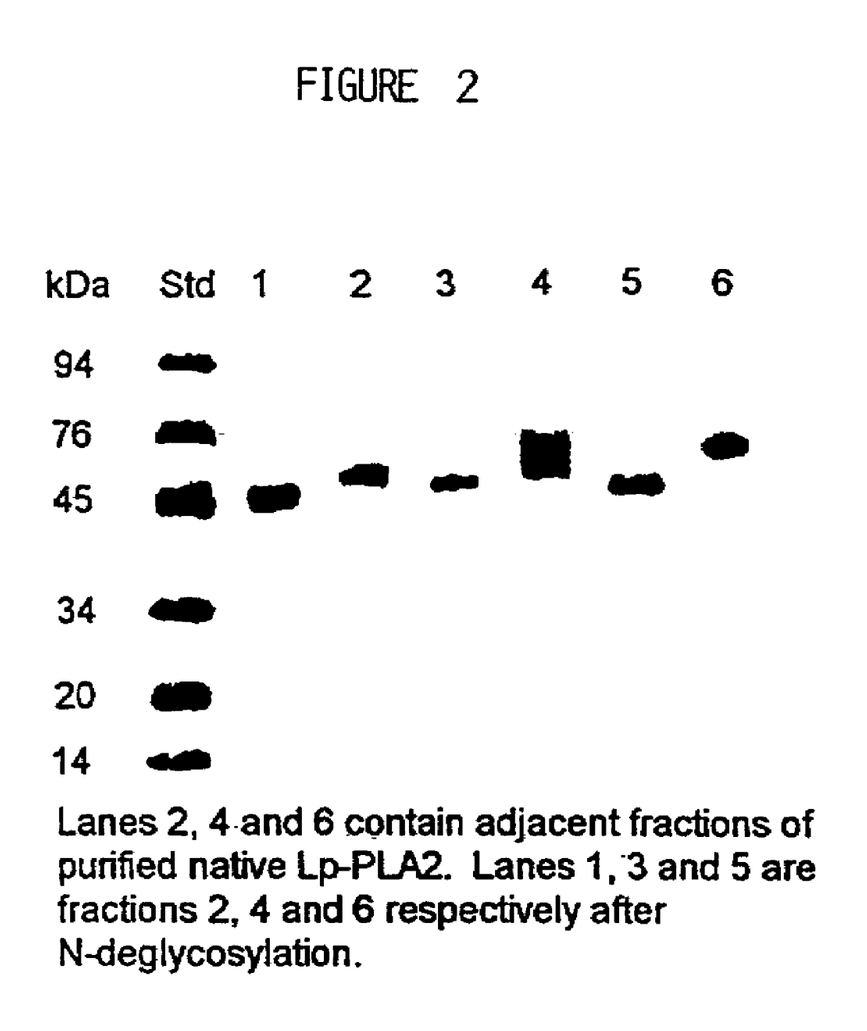
FIG. 2 is an analysis the purified Lp-PLA$_2$ material of Example 4 following separation by polyacrylamide gel electrophoresis. Lanes 2, 4 and 6 contain adjacent fractions of purified native Lp-PLA$_2$. Lanes 1, 3 and 5 are fractions 2, 4 and 6 respectively after N-deglycosylation.

The dialysed Lp-PLA$_2$ was submitted to anion exchange chromatography on a mono Q column (Pharmacia) using 50 mM Tris, 10 mM CHAPS, pH=8.0 with a NaCl gradient from zero to 0.3 M. The Lp-PLA$_2$ fractions obtained from the mono Q column were applied directly to a Hi Trap Blue cartridge (Pharmacia). The cartridge was washed with 50 mM Tris, 10 mM CHAPS, 0.5 M NaCl, pH=8.0 until the absorbance of the eluate (280 nm) was zero. Lp-PLA$_2$ was then eluted using 50 mM Tris, 10 mM CHAPS, 1.5 M NaCl, pH=8.0. This gave Lp-PLA$_2$ which is greater than 95% pure as shown in FIG. 2. This also demonstrates that the native enzyme is extensively glycosylated.

5. Enzyme Sequence

The purity of the final enzyme preparation was verified by five criteria 1) SDS-polyacrylamide gel electrophoresis gave one band for both native and de-glycosylated forms. 2) Reverse phase high pressure liquid chromatography (RP-HPLC) gave a single peak, 3) The intact preparation gave no results by protein sequencing, implying that the protein was N-terminally blocked and free of any contaminants with open N-terminals, 4) By laser desorbtion mass spectometry only one broad peak was observed with de-glycosylated protein, and 5) none of the sections of extended peptide data from sequencing gave any databse matches indicative of contaminating proteins. Three cleavage strategies were used to obtain internal sequence information; trypsin (after deglycosylation), cyanogen bromide (methionine cleavage) and BNPS-Skatol (tryptophan cleavage). The resulting peptides were separated by RP-HPLC, collected and sequenced. The accumulated sequence data allowed several extended stretches of primary structure of the Lp-PLA2 enzyme to be verified. These are shown below as Peptides 1, 2, 3 and 4 (SEQ ID Nos 1 to 4). When searched against the National Centre for Biotechnological information (NCBI) non-redundant peptide sequence databases no high similarity matches were obtained. Estimation of the molecular weight of pure, de-glycosylated protein by laser desorption mass spectometry gives values in the region of 45-47 kDa (separately 45 kDa and 4647 kDa), indicating that the sequences constitute approximately 15 to 20% of the protein.

6. Gene Sequence

Three expressed sequence tags (ESTs) from human cDNA libraries have been found to have extensive alignments with the Peptide Sequences 1 to 3. These EST's are shown below as Nucleotide Sequences 1 to 3 (SEQ ID Nos: 5 to 7) Nucleotide Sequence 1 is a 420 base sequence derived from a human foetal spleen library. Nucleotide Sequence 2 is a 379 base sequence derived from a 12-week human embryo library. Nucleotide Sequence 3 is a 279 base sequence derived from a T-cell lymphoma library. The identities at both the nucleic acid and amino acid level justified an overlapping alignment of the cDNA of all three ESTs, Nucleotide Sequences 3 (bases 1-278), 1 (bases 1-389) (in reverse orientation) and 2 (bases 1-304) with the Peptide Sequences 1, 2 and 3 (partially). Beyond these limits, the poor resolution of the raw sequence data precludes accurate base calling.

There are two remaining unassigned peptide sections from Peptides 3 and 4, both of which are expected to be present in the complete protein. Q-Y-I-N-P-A-V-(SEQ ID No:12) and W-L-M-G-N-I-L-R-L-L-F-G-S-M-T-T-P-A-N-(SEQ ID No:4).

7. Isolation of Full-length Lp-PLA$_2$ cDNA

The full DNA sequence was determined for the clone (HLTA145) from which the Lymphoma EST (SEQ ID No:7) was derived, giving a total of 572 bases; SEQ ID No:8. There is one base difference between this sequence and the EST (between bases 1 to 256 of the EST); at position 27 of HLTA145 there is an A compared with a T in the EST. This would cause a coding change; L in HLTA145 compared with F in the EST. Clone HLTA145 was used as a radiolabelled probe to screen the Lymphoma cDNA library in order to isolate the full-length Lp-PLA$_2$ clone. The library was prepared in the bacteriophage λ vector, Unizap XR (Stratagene).

Preparation of the Filters for Screening

The library was plated out at a density of 20,000 plaques per 150 mm petri dish onto *E. coli* XL-1 Blue host cells (ie. 200,000 plaques on 10 dishes). An overnight of XL-1 Blue was prepared in 100 mls LB/0.2% w/v Maltose/10 mM MgSO$_4$ The cells were pelleted, resuspended in 50 mls 10 mM MgSO$_4$ and stored on ice. 180 µl of the library bacteriophage stock (23,400 pfu's) were added to 7 mls XL-1 Blue cells, mixed and divided into 10 aliqouts of 615 µl. The 10 tubes were incubated at 37° C. for 30 minutes. 7 mls of molten (@45° C.) top agarose (0.7% w/v agarose in LB) were added, mixed well and poured onto 150 mm LB agar plates (1.5% w/v agar in LB). The plates were inverted and incubated at 37° C. for approximately 7.5 hours. The plates were held at 4° C. until needed.

The plaques were transfered to 132 mm Hybond-N nylon filters (Amersham International) by laying the filters on the plates for 2 minutes (4 minutes for the duplicate). The DNA's on the filters were denatured for 2 minutes (0.5M NaCl, 1.5M NaOH), neutralised for 4 minutes (1.5M NaCl, 1.0M Tris pH7.4) and the filters placed on 2×SSC for 1 minute. The filters were then dried and the DNA crosslinked to the filter using a Stratalinker UV 2400 (Stratagene) at 120,000 µJoules/cm$^2$.

The filters were pre-hybridised in 1 mM EDTA, 0.5M NaHPO$_4$, 7% SDS (Church, G M. and Gilbert, W. (1984) PNAS USA 81 p1991-1995) in a Techne HB2 hybridisation oven at 55° C. for 3 hours. Each bottle contained 2 filters and 25 mls prehybridization solution.

Preparation of the Radiolabelled Probe

The probe cDNA (from HLTA 145) was excised from pBluescript II SK+/− as an approximately 600 bp EcoRI-XhoI fragment and approximately 100 ng of gel purified fragment were labelled using 1.2 MBq $^{32}$P dATP and 1.2 MBq $^{32}$P dCTP by PCR labelling using Taq DNA polymerase (Boehringer Mannheim) and primers designed to prime at the 5' and 3' ends of the EST sequence. The labelling reaction was carried out in a total volume of 200 µl and included unlabelled dNTP's at the following concentrations:—

| dATP | 20 µM |
|------|-------|
| dCTP | 20 µM |
| dGTP | 200 µM |
| dTTP | 200 µM |

The PCR reaction was carried out over 35 cycles of:—
- 94° C. for 30 s
- 60° C. for 30 s
- 72° C. for 30 s Screening The radiolabelled probe was denatured at 98° C. for 5 minutes and divided into 10 aliquots of 20%1. One aliquot was added per hybridisation bottle. Hybridisation was carried out over 16 hours at 55° C. The filters were washed at 60° C. (2×10 minutes) with 0.1% w/v SDS, 0.1×SSC (50 mls per wash per bottle). The filters were autoradiographed and the films (Fuji Medical X-Ray Film) developed after 5 days exposure.

Duplicate positives were progressed to a secondary screen. The plaques were cored out into 1 ml SM (100 mM NaCl, 10 mM MgSO$_4$, 1M Tris, pH7.4), titrated and plated onto 90 mm petri dishes at between 20 and 200 pfu's per dish. The secondary screen was carried out as described for the primary screen except the filters were washed at 65° C. The autoradiographs were developed after 16 hours exposure.

DNA Sequencing

The duplicated positive clones from the secondary screen were excised from the λ Unizap XR bacteriophage vector into the Bluescript phagemid (according to the Stratagene manual) for characterisation. One of the clones, carrying an insert of approximately 1.5 kb, was sequenced on both strands (using the USB Sequenase 2.0 DNA sequencing kit) by primer walking (SEQ ID No:9). The cDNA has an open reading frame with the potential to code for a polypeptide of 441 amino acids.

The 3' region of the full-length cDNA aligns with the HLTA145 sequence with the exception of 3 mismatches (see below). The predicted polypeptide sequence of the lymphoma Lp-PLA$_2$ is shown as SEQ ID No:9.

Inspection of the full length cDNA (SEQ ID No:9) reveals probable errors in Peptide 3. One of these errors in the assignment of continuity of V-M which is incompatible with the perfect sequence match with the cDNA after this position. It seems likely that a short peptide containing the sequence Q-Y-I-N-P- (SEO ID No: 13) co-purified with a longer cyanogen bromide partial cleavage peptide and, by being present in greater quantity, was assigned as the major sequence and contiguous with the subsequent amino acids. The remaining section of Peptide 3 and the whole of Peptide 4 can be identified in the predicted full length enzyme sequence (SEQ ID No:9). It thus seems likely that Peptide 3 is in fact two separate Peptides 5 (SEQ ID No:10), and 6 (SEQ ID No:11). The second probable error has occurred in the transcription from the raw data for Peptide 3 which upon checking was consistent with Peptide 5 having the sequence of Q-Y-I-N-P-V-A-(SEQ ID No:10), rather than Q-Y-I-N-P-A-V-(SEQ ID No:12).

The 3 base differences are as follows:—
1) T at 859 is A in HLTA145; aminoacid change F in full-length, L in HLTA 145. (Note that the original EST is identical with the full-length cDNA at position 859).
2) C at 1173 is T in HLTA145; aminoacid change A in full-length, V in HLTA145.
3) T at 1203 is C in HLTA145; aminoacid change L in full-length, S in HLTA145.

The peptide data and the Foetal Spleen EST sequence (SEQ ID No:5) support the full-length cDNA sequence for differences (2) and (3) although the Human Embryo EST (SEQ ID No:6) is identical to the Lymphoma EST (SEQ ID No:7) at position 1173. The Human Embryo EST (SEQ ID No:6) has a further difference (4) corresponding to position 1245 in the full-length Lymphoma sequence (SEQ ID No:9) (comparison between bases 2 to 304 of the Human Embryo EST and the full-length Lymphoma cDNA).

4) A at 1245 is T in the Embryo EST (SEQ ID No:6)(amino acid change D to V in the Embryo EST). Peptide data covering this region supports the Lymphoma DNA sequence (SEQ ID No:9).

The Lp-PLA$_2$ DNA sequence from 848 to 1361 of SEQ ID No:9 (amino acid residues 271 to 441 of SEQ ID No:9) is the region for which all major data sets agree substantially, ie. the peptide data, the Foetal spleen, full-length Lymphoma and it includes the known active site and is therefore believed to be a significant characterising region for the Lp-PLA$_2$ enzyme.

The predicted MW for the full reading frame is 50090. This in in exess of that determined for the de-glycosylated, purified protein but post-translational events could account for this discrepancy. The most likely of these are the removal of an N-terminal signal peptide and/or limited proteolytic degradation of the protein C-terminal. The latter could occur in-vivo, during purification, or under the conditions of de-glycosylation.

Diagnostic Method

A sample of blood is taken from a patient, the plasma/serum sample prepared and passed through a dextran sulphate column pre-equilibrated with 0.9% (w\v) NaCl solution. Following washes with the same salt solution Lp-PLA$_2$ is eluted with a 4.1% (w\v) NaCl solution. Heparin agarose columns can also be used with the wash and elution solutions containing 0.7% and 2.9% NaCl, respectively. Enzyme present in the sample is determined by assaying for either (a) Enzyme Activity:

The substrate (A) (see structure in 1) is used to assay Lp-PLA$_2$ activity by monitoring the absorbance change at 400 nm. Purified enzyme is pre-incubated at 37° C. and substrate (50 µM) is added after 5 minutes. The absorbance change at 400 nm is monitored for 20 minutes. This substrate has previously been reported as a substrate for classical calcium-dependent PLA$_2$s. (Washburn, W. N. and Dennis, E. A., *J. Amer Chem. Soc.,* 1990, 112, 2040-2041); or (b) Protein Content Total protein content (i.e. enzyme content) can be determined using polyclonal antiserum raised against purified human Lp-PLA$_2$. The antisera recognises both native and glycosylated enzyme as measured by immunoprecipitation of activity and Western Blot analysis.

Polyclonal antiserum was prepared as follows. Immunisation of rabbits involved mixing 0.5 ml of purified human Lp-PLA$_2$ (=100 µg) with an equal volume of Freund's complete adjuvant. The final emulsion was given subcutaneously in 4×0.25 ml injections. Boosting using a Freund's incomplete adjuvant\antigen mixture (4×0.25 ml subcut.; dosage=50 µg) took place 4 weeks later. Adequate titre was evident at between 6-8 weeks from initial injection.

SEQUENCE DATA

```
SEQ. ID. No: 1 -Peptide 1
-M-L-K-L-K-G-D-I-D-S-N-A-A-I-D-L-S-N-K-A-S-L-A-F-L-Q-K-H-L-G-
L-H-K-D-F-D-Q-

SEQ. ID. No: 2 - Peptide 2
-W-M-F-P-L-G-D-E-V-Y-S-R-I-P-Q-P-L-F-F-I-N-S-E-Y-F-Q-Y-P-A-N-

SEQ. ID. No: 3 - Peptide 3
-Q-Y-I-N-P-A-V-M-I-T-I-R-G-S-V-H-Q-N-F-A-D-F-T-F-A-T-G-

SEQ. ID. No: 4 - Peptide 4
-W-L-M-G-N-I-L-R-L-L-F-G-S-M-T-T-P-A-N

SEQ. ID. No: 5 - Nucleotide Sequence 1
    1 AAAAAACCTA TTTTAATCCT AATTGTATTT CTCTATTCCT GAAGAGTTCT

51 GTAACATGAT GTGTTGATTG GTTGTGTTAA TGTTGGTCCC TGGAATAAGA

101 TTCTCATCAT CTCCTTCAAT CAAGCAGTCC CACTGATCAA AATCTTTATG

151 AAGTCCTAAA TGCTTTTGTA AGAATGCTAA TGAAGCTTTG TTGCTAAGAT

201 CAATAGCTGC ATTTGAATCT ATGTCTCCCT TTAATTTGAG CATGTGTCCA

251 ATTATTTTGC CAGTNGCAAA AGTGAAGTCA GCAAAATTCT GGTGGACTGA

301 ACCCCTGATT GTAATCATCT TTCTTTCTTT ATCAGGTGAG TAGCATTTTT

351 TCATTTTTAT GATATTAGCA GGATATTGGA AATATTCAGN GTTGNTAAAA

401 AGNGGNGGCT GAGGGATTCT

SEQ. ID. No: 6 - Nucleotide Sequence 2
    1 TGCTAATATC ATAAAAATGA AAAAATGCTA CTCACCTGAT AAAGAAAGAA

51 AGATGATTAC AATCAGGGGT TCAGTCCACC AGANTTTTGC TGACTTCACT

101 TTTGCAACTG GCAAAATAAT TGGACACATG CTCAAATTAA AGGGAGACAT

151 AGATICAAAT GTAGCTATTG ATCTTAGCAA CAAAGCTTCA TTAGCATTCT

201 TACAAAAGCA TTTAGGACTT CATAAAGATT TTGTTCAGTG GGACTGCTTG

251 ATTGAAGGAG ATGATGAGAA TCTTATTCCA GGGACCAACA TTAACACAAC

301 CAATTCAACA CATCATGTTT ACAGAACTTC TTCCAGGGAA TAGGAGGAAA

351 TACAATTGGG GTTTAAAATA GGTTTTTTT

SEQ. ID. No: 7 - Nucleotide Sequence 3
    1 GAAGAATGCA TTAGATTTAA AGTTTGATAT GGAACAACTG AAGGACTCTA

51 TTGATAGGGA AAAAATAGCA GTAATTGGAC ATTCTTTTGG TGGAGCAACG

101 GTTATTCAGA CTCTTAGTGA AGATCAGAGA TTCAGATGTG GTATTGCCCT

151 GGATGCATGG ATGTTTCCAC TGGGTGATGA AGTATATTCC AGAATTCCTC

201 AGCCCCTCTT TTTTATCAAC TCTGAATATT TCCAATATCC TGCTAATATC

251 ATAAAANTGG AAAAATGCTA CTCACCTGG

Seq. ID. No: 8 - DNA sequence of HLTA145
```

-continued

```
         10         20         30         40         50
AAAATAGCAG TAATTGGACA TTCTTTAGGT GGAGCAACGG TTATTCAGAC 60         70         80         90        100
TCTTAGTGAA GATCAGAGAT TCAGATGTGG TATTGCCCTG GATGCATGGA 110        120        130        140        150
TGTTTCCACT GGGTGATGAA GTATATTCCA GAATTCCTCA GCCCCTCTTT 160        170        180        190        200
TTTATCAACT CTGAATATTT CCAATATCCT GCTAATATCA TAAAAATGAA 210        220        230        240        250
AAAATGCTAC TCACCTGATA AAGAAAGAAA GATGATTACA ATCAGGGGTT 260        270        280        290        300
CAGTCCACCA GAATTTTGCT GACTTCACTT TTGCAACTGG CAAATAATT 310        320        330        340        350
GGACACATGC TCAAATTAAA GGGAGACATA GATTCAAATG TAGCTATTGA 360        370        380        390        400
TCTTAGCAAC AAAGCTTCAT CAGCATTCTT ACAAAAGCAT TTAGGACTTC 410        420        430        440        450
ATAAAGATTT TGATCAGTGG GACTGCTTGA TTGAAGGAGA TGATGAGAAT 460        470        480        490        500
CTTATTCCAG GGACCAACAT TAACACAACC AATCAACACA TCATGTTACA 510        520        530        540        550
GAACTCTTCA GGAATAGAGA AATACAATTA GGATTAAAAT AGGTTTTTTA 560        570
AAAAAAAAAA AAAAAAACT CG
```

SEQ. ID. No: 9 - cDNA Sequence of Lymphoma Lp-PLA$_2$

```
         10         20         30         40         50
TGAGAGACTAAGCTGAAACTGCTGCTCAGCTCCCAAGATGGTGCCACCCA
                                      M  V  P  P  K 60         70         80         90        100
AATTGCATGTGCTTTTCTGCCTCTGCGGCTGCCTGGCTGTGGTTTATCCT
 L  H  V  L  F  C  L  C  G  C  L  A  V  V  Y  P 110        120        130        140        150
TTTGACTGGCAATACATAAATCCTGTTGCCCATATGAAATCATCAGCATG
 F  D  W  Q  Y  I  N  P  V  A  H  M  K  S  S  A  W 160        170        180        190        200
GGTCAACAAAATACAAGTACTGATGGCTGCTGCAAGCTTTGGCCAAACTA
 V  N  K  I  Q  V  L  M  A  A  A  S  F  G  Q  T  K 210        220        230        240        250
AAATCCCCCGGGGAAATGGGCCTTATTCCGTTGGTTGTACAGACTTAATG
  I  P  R  G  N  G  P  Y  S  V  G  C  T  D  L  M 260        270        280        290        300
TTTGATCACACTAATAAGGGCACCTTCTTGCGTTTATATTATCCATCCCA
 F  D  H  T  N  K  G  T  P  L  R  L  Y  Y  P  S  Q 310        320        330        340        350
AGATAATGATCGCCTTGACACCCTTTGGATCCCAAATAAAGAATATTTTT
 D  N  D  R  L  D  T  L  W  I  P  N  K  E  Y  F  W 360        370        380        390        400
GGGGTCTTAGCAAATTCTTGGAACACACTGGCTTATGGGCAACATTTTG
  G  L  S  K  F  L  G  T  H  W  L  M  G  N  I  L 410        420        430        440        450
AGGTTACTCTTTGGTTCAATGACAACTCCTGCAAACTGGAATTCCCCTCT
 R  L  L  F  G  S  M  T  T  P  A  N  W  N  S  P  L 460        470        480        490        500
GAGGCCTGGTGAAAAATATCCACTTGTTGTTTTTCTCATGGTCTTGGGG
 R  P  G  E  K  Y  P  L  V  V  F  S  H  G  L  G  A 510        520        530        540        550
CATTCAGGACACTTTATTCTGCTATTGGCATTGACCTGGCATCTCATGGG
  F  R  T  L  Y  S  A  I  G  I  D  L  A  S  H  G
```

```
        560         570         580         590         600
TTTATAGTTGCTGCTGTAGAACACAGAGATAGATCTGCATCTGCAACTTA
 F  I  V  A  A  V  E  H  R  D  R  S  A  S  A  T  Y 610         620         630         640         650
CTATTTCAAGGACCAATCTGCTGCAGAAATAGGGGACAAGTCTTGGCTCT
 Y  F  K  D  Q  S  A  A  E  I  G  D  K  S  W  L  Y 660         670         680         690         700
ACCTTAGAACCCTGAAACAAGAGGAGGAGACACATATACGAAATGAGCAG
  L  R  T  L  K  Q  E  E  E  T  H  I  R  N  E  Q 710         720         730         740         750
GTACGGCAAAGAGCAAAAGAATGTTCCCAAGCTCTCAGTCTGATTCTTGA
 V  R  Q  R  A  K  E  C  S  Q  A  L  S  L  I  L  D 760         770         780         790         800
CATTGATCATGGAAAGCCAGTGAAGAATGCATTAGATTTAAAGTTTGATA
  I  D  H  G  K  P  V  K  N  A  L  D  L  K  F  D  M 810         820         830         840         850
TGGAACAACTGAAGGACTCTATTGATAGGGAAAAAATAGCAGTAATTGGA
  E  Q  L  K  D  S  I  D  R  E  K  I  A  V  I  G 860         870         880         890         900
CATTCTTTTGGTGGAGCAACGGTTATTCAGACTCTTAGTGAAGATCAGAG
 H  S  F  G  G  A  T  V  I  Q  T  L  S  E  D  Q  R 910         920         930         940         950
ATTCAGATGTGGTATTGCCCTGGATGCATGGATGTTTCCACTGGGTGATG
 F  R  C  G  I  A  L  D  A  W  M  F  P  L  G  D  E 960         970         980         990        1000
AAGTATATTCCAGAATTCCTCAGCCCCTCTTTTTTATCAACTCTGAATAT
  V  Y  S  R  I  P  Q  P  L  F  F  I  N  S  E  Y 1010        1020        1030        1040        1050
TTCCAATATCCTGCTAATATCATAAAAATGAAAAAATGCTACTCACCTGA
 F  Q  Y  P  A  N  I  I  K  M  K  K  C  Y  S  P  D 1060        1070        1080        1090        1100
TAAAGAAAGAAAGATGATTACAATCAGGGGTTCAGTCCACCAGAATTTTG
  K  E  R  K  M  I  T  I  R  G  S  V  H  Q  N  F  A 1110        1120        1130        1140        1150
CTGACTTCACTTTTGCAACTGGCAAAATAATTGGACACATGCTCAAATTA
  D  F  T  F  A  T  G  K  I  I  G  H  M  L  K  L 1160        1170        1180        1190        1200
AAGGGAGACATAGATTCAAATGCAGCTATTGATCTTAGCAACAAAGCTTC
 K  G  D  I  D  S  N  A  A  I  D  L  S  N  K  A  S 1210        1220        1230        1240        1250
ATTAGCATTCTTACAAAAGCATTTAGGACTTCATAAAGATTTTGATCAGT
 L  A  F  L  Q  K  H  L  G  L  H  K  D  F  D  Q  W 1260        1270        1280        1290        1300
GGGACTGCTTGATTGAAGGAGATGATGAGAATCTTATTCCAGGGACCAAC
  D  C  L  I  E  G  D  D  E  N  L  I  P  G  T  N 1310        1320        1330        1340        1350
ATTAACACAACCAATCAACACATCATGTTACAGAACTCTTCAGGAATAGA
 I  N  T  T  N  Q  H  I  M  L  Q  N  S  S  G  I  E

1360
GAAATACAATT
 K  Y  N

SEQ. ID. No: 10 -Peptide 5
-Q-Y-I-N-P-V-A-

SEQ. ID. No: 11 -Peptide 6
-M-I-T-I-R-G-S-V-H-Q-N-F-A-D-F-T-F-A-T-G-
```

The invention claimed is:

1. An active naturally occurring lipoprotein associated phospholipase A2 at least 95% pure relative to other protein contaminants and encoded by a polynucleotide having at least 95% sequence identity with SEQ ID NO:9 over the entire length of SEQ ID NO:9, wherein said lipoprotein associated phospholipase A2 is capable of hydrolyzing the sn-2 ester of an oxidatively modified phosphatidylcholine.

2. The lipoprotein associated phospholipase A2 according to claim 1, having a molecular weight of from about 45 kDa to about 50 kDa and comprising at least one sequence selected from the following: SEQ ID NO: 1, 2, and 4.

* * * * *

UNITED STATES PATENT AND TRADEMARK OFFICE
CERTIFICATE OF CORRECTION

PATENT NO. : 7,314,742 B2
APPLICATION NO. : 11/108519
DATED : January 1, 2008
INVENTOR(S) : MacPhee et al.

Page 1 of 1

It is certified that error appears in the above-identified patent and that said Letters Patent is hereby corrected as shown below:

Title page Item (73) Assignee: Add SmithKline Beecham p.l.c.

Signed and Sealed this

Thirtieth Day of December, 2008

JON W. DUDAS
*Director of the United States Patent and Trademark Office*

SEQUENCE LISTING

<160> NUMBER OF SEQ ID NOS: 14

<210> SEQ ID NO 1
<211> LENGTH: 37
<212> TYPE: PRT
<213> ORGANISM: Homo sapien

<400> SEQUENCE: 1

Met Leu Lys Leu Lys Gly Asp Ile Asp Ser Asn Ala Ala Ile Asp Leu
1               5                   10                  15

Ser Asn Lys Ala Ser Leu Ala Phe Leu Gln Lys His Leu Gly Leu His
            20                  25                  30

Lys Asp Phe Asp Gln
        35

<210> SEQ ID NO 2
<211> LENGTH: 30
<212> TYPE: PRT
<213> ORGANISM: Homo sapien

<400> SEQUENCE: 2

Trp Met Phe Pro Leu Gly Asp Glu Val Tyr Ser Arg Ile Pro Gln Pro
1               5                   10                  15

Leu Phe Phe Ile Asn Ser Glu Tyr Phe Gln Tyr Pro Ala Asn
            20                  25                  30

<210> SEQ ID NO 3
<211> LENGTH: 27
<212> TYPE: PRT
<213> ORGANISM: Homo sapien

<400> SEQUENCE: 3

Gln Tyr Ile Asn Pro Ala Val Met Ile Thr Ile Arg Gly Ser Val His
1               5                   10                  15

Gln Asn Phe Ala Asp Phe Thr Phe Ala Thr Gly
            20                  25

<210> SEQ ID NO 4
<211> LENGTH: 19
<212> TYPE: PRT
<213> ORGANISM: Homo sapien

<400> SEQUENCE: 4

Trp Leu Met Gly Asn Ile Leu Arg Leu Leu Phe Gly Ser Met Thr Thr
1               5                   10                  15

Pro Ala Asn

<210> SEQ ID NO 5
<211> LENGTH: 420
<212> TYPE: DNA
<213> ORGANISM: Homo sapien
<220> FEATURE:
<221> NAME/KEY: misc_feature
<222> LOCATION: 265, 390, 395, 403, 406
<223> OTHER INFORMATION: n = A,T,C or G

<400> SEQUENCE: 5
aaaaaaccta ttttaatcct aattgtattt ctctattcct gaagagttct gtaacatgat      60
gtgttgattg gttgtgttaa tgttggtccc tggaataaga ttctcatcat ctccttcaat     120
caagcagtcc cactgatcaa aatctttatg aagtcctaaa tgcttttgta agaatgctaa     180

```
tgaagctttg ttgctaagat caatagctgc atttgaatct atgtctccct ttaatttgag    240
catgtgtcca attattttgc cagtngcaaa agtgaagtca gcaaaattct ggtggactga    300
acccctgatt gtaatcatct ttctttcttt atcaggtgag tagcattttt tcatttttat    360
gatattagca ggatattgga aatattcagn gttgntaaaa agnggnggct gagggattct    420
```

<210> SEQ ID NO 6
<211> LENGTH: 379
<212> TYPE: DNA
<213> ORGANISM: Homo sapien
<220> FEATURE:
<221> NAME/KEY: misc_feature
<222> LOCATION: 84
<223> OTHER INFORMATION: n = A,T,C or G

<400> SEQUENCE: 6

```
tgctaatatc ataaaaatga aaaaatgcta ctcacctgat aaagaaagaa agatgattac     60
aatcaggggt tcagtccacc agantttgc tgacttcact tttgcaactg gcaaaataat    120
tggacacatg ctcaaattaa agggagacat agattcaaat gtagctattg atcttagcaa    180
caaagcttca ttagcattct tacaaaagca tttaggactt cataaagatt ttgttcagtg    240
ggactgcttg attgaaggag atgatgaaa tcttattcca gggaccaaca ttaacacaac    300
caattcaaca catcatgttt acagaacttc ttccagggaa taggaggaaa tacaattggg    360
gtttaaaata ggtttttttt                                                379
```

<210> SEQ ID NO 7
<211> LENGTH: 279
<212> TYPE: DNA
<213> ORGANISM: Homo sapien
<220> FEATURE:
<221> NAME/KEY: misc_feature
<222> LOCATION: 257
<223> OTHER INFORMATION: n = A,T,C or G

<400> SEQUENCE: 7

```
gaagaatgca ttagatttaa agtttgatat ggaacaactg aaggactcta ttgataggga     60
aaaaatagca gtaattggac attcttttgg tggagcaacg gttattcaga ctcttagtga    120
agatcagaga ttcagatgtg gtattgccct ggatgcatgg atgtttccac tgggtgatga    180
agtatattcc agaattcctc agcccctctt ttttatcaac tctgaatatt ccaatatcc     240 tgctaatatc ataaaantgg aaaaatgcta ctcacctgg                           279
```

<210> SEQ ID NO 8
<211> LENGTH: 572
<212> TYPE: DNA
<213> ORGANISM: Homo sapien

<400> SEQUENCE: 8

```
aaaatagcag taattggaca ttctttaggt ggagcaacgg ttattcagac tcttagtgaa     60
gatcagagat tcagatgtgg tattgccctg gatgcatgga tgtttccact gggtgatgaa    120
gtatattcca gaattcctca gcccctcttt tttatcaact ctgaatattt ccaatatcct    180
gctaatatca taaaaatgaa aaaatgctac tcacctgata aagaaagaaa gatgattaca    240 atcagggggtt cagtccacca gaattttgct gacttcactt ttgcaactgg caaaataatt    300
ggacacatgc tcaaattaaa gggagacata gattcaaatg tagctattga tcttagcaac    360
aaagcttcat cagcattctt acaaaagcat ttaggactt ataagagattt tgatcagtgg    420
```

| | |
|---|---|
| gactgcttga ttgaaggaga tgatgagaat cttattccag ggaccaacat taacacaacc | 480 |
| aatcaacaca tcatgttaca gaactcttca ggaatagaga aatacaatta ggattaaaat | 540 |
| aggttttta aaaaaaaaaa aaaaaaaact cg | 572 |

<210> SEQ ID NO 9
<211> LENGTH: 1361
<212> TYPE: DNA
<213> ORGANISM: Homo sapien

<400> SEQUENCE: 9

| | |
|---|---|
| tgagagacta agctgaaact gctgctcagc tcccaagatg gtgccaccca aattgcatgt | 60 |
| gcttttctgc ctctgcggct gcctggctgt ggtttatcct tttgactggc aatacataaa | 120 |
| tcctgttgcc catatgaaat catcagcatg ggtcaacaaa atacaagtac tgatggctgc | 180 |
| tgcaagcttt ggccaaacta aaatcccccg gggaaatggg ccttattccg ttggttgtac | 240 |
| agacttaatg tttgatcaca ctaataaggg caccttcttg cgtttatatt atccatccca | 300 |
| agataatgat cgccttgaca ccctttggat cccaaataaa gaatattttt ggggtcttag | 360 |
| caaatttctt ggaacacact ggcttatggg caacattttg aggttactct ttggttcaat | 420 |
| gacaactcct gcaaactgga attcccctct gaggcctggt gaaaaatatc cacttgttgt | 480 |
| ttttctcat ggtcttgggg cattcaggac actttattct gctattggca ttgacctggc | 540 |
| atctcatggg tttatagttg ctgctgtaga acacagagat agatctgcat ctgcaactta | 600 |
| ctatttcaag gaccaatctg ctgcagaaat aggggacaag tcttggctct accttagaac | 660 |
| cctgaaacaa gaggaggaga cacatatacg aaatgagcag gtacggcaaa gagcaaaaga | 720 |
| atgttcccaa gctctcagtc tgattcttga cattgatcat ggaaagccag tgaagaatgc | 780 |
| attagattta agtttgata tggaacaact gaaggactct attgataggg aaaaaatagc | 840 |
| agtaattgga cattcttttg gtggagcaac ggttattcag actcttagtg aagatcagag | 900 |
| attcagatgt ggtattgccc tggatgcatg gatgtttcca ctgggtgatg aagtatattc | 960 |
| cagaattcct cagcccctct tttttatcaa ctctgaatat ttccaatatc ctgctaatat | 1020 |
| cataaaaatg aaaaaatgct actcacctga taaagaaaga aagatgatta caatcagggg | 1080 |
| ttcagtccac cagaattttg ctgacttcac ttttgcaact ggcaaaataa ttggacacat | 1140 |
| gctcaaatta aagggagaca tagattcaaa tgcagctatt gatcttagca acaaagcttc | 1200 |
| attagcattc ttacaaaagc atttaggact tcataaagat tttgatcagt gggactgctt | 1260 |
| gattgaagga gatgatgaga atcttattcc agggaccaac attaacacaa ccaatcaaca | 1320 |
| catcatgtta cagaactctt caggaataga gaaatacaat t | 1361 |

<210> SEQ ID NO 10
<211> LENGTH: 7
<212> TYPE: PRT
<213> ORGANISM: Homo sapien

<400> SEQUENCE: 10

Gln Tyr Ile Asn Pro Val Ala
 1               5

<210> SEQ ID NO 11
<211> LENGTH: 20
<212> TYPE: PRT
<213> ORGANISM: Homo sapien

<400> SEQUENCE: 11

```
Met Ile Thr Ile Arg Gly Ser Val His Gln Asn Phe Ala Asp Phe Thr
 1               5                  10                  15

Phe Ala Thr Gly
            20
```

<210> SEQ ID NO 12
<211> LENGTH: 7
<212> TYPE: PRT
<213> ORGANISM: Homo sapien

<400> SEQUENCE: 12

```
Gln Tyr Ile Asn Pro Ala Val
 1               5
```

<210> SEQ ID NO 13
<211> LENGTH: 5
<212> TYPE: PRT
<213> ORGANISM: Homo sapien

<400> SEQUENCE: 13

```
Gln Tyr Ile Asn Pro
 1               5
```

<210> SEQ ID NO 14
<211> LENGTH: 441
<212> TYPE: PRT
<213> ORGANISM: Homo sapien

<400> SEQUENCE: 14

```
                                    Met Val Pro Pro Lys Leu
                                     1               5

His Val Leu Phe Cys Leu Cys Gly Cys Leu Ala Val Val Tyr Pro Phe
            10                  15                  20

Asp Trp Gln Tyr Ile Asn Pro Val Ala His Met Lys Ser Ser Ala Trp
            25                  30                  35

Val Asn Lys Ile Gln Val Leu Met Ala Ala Ala Ser Phe Gly Gln Thr
            40                  45                  50

Lys Ile Pro Arg Gly Asn Gly Pro Tyr Ser Val Gly Cys Thr Asp Leu
55                  60                  65                  70

Met Phe Asp His Thr Asn Lys Gly Thr Phe Leu Arg Leu Tyr Pro
                75                  80                  85

Ser Gln Asp Asn Asp Arg Leu Asp Thr Leu Trp Ile Pro Asn Lys Glu
            90                  95                  100

Tyr Phe Trp Gly Leu Ser Lys Phe Leu Gly Thr His Trp Leu Met Gly
            105                 110                 115

Asn Ile Leu Arg Leu Leu Phe Gly Ser Met Thr Thr Pro Ala Asn Trp
            120                 125                 130

Asn Ser Pro Leu Arg Pro Gly Glu Lys Tyr Pro Leu Val Val Phe Ser
135                 140                 145                 150

His Gly Leu Gly Ala Phe Arg Thr Leu Tyr Ser Ala Ile Gly Ile Asp
            155                 160                 165

Leu Ala Ser His Gly Phe Ile Val Ala Val Glu His Arg Asp Arg
            170                 175                 180

Ser Ala Ser Ala Thr Tyr Tyr Phe Lys Asp Gln Ser Ala Ala Glu Ile
            185                 190                 195

Gly Asp Lys Ser Trp Leu Tyr Leu Arg Thr Leu Lys Gln Glu Glu Glu
            200                 205                 210

Thr His Ile Arg Asn Glu Gln Val Arg Gln Arg Ala Lys Glu Cys Ser
```

```
                                    -continued
215                 220                 225                 230
Gln Ala Leu Ser Leu Ile Leu Asp Ile Asp His Gly Lys Pro Val Lys
            235                 240                 245

Asn Ala Leu Asp Leu Lys Phe Asp Met Glu Gln Leu Lys Asp Ser Ile
            250                 255                 260

Asp Arg Glu Lys Ile Ala Val Ile Gly His Ser Phe Gly Gly Ala Thr
            265                 270                 275

Val Ile Gln Thr Leu Ser Glu Asp Gln Arg Phe Arg Cys Gly Ile Ala
            280                 285                 290

Leu Asp Ala Trp Met Phe Pro Leu Gly Asp Glu Val Tyr Ser Arg Ile
295                 300                 305                 310

Pro Gln Pro Leu Phe Phe Ile Asn Ser Glu Tyr Phe Gln Tyr Pro Ala
            315                 320                 325

Asn Ile Ile Lys Met Lys Lys Cys Tyr Ser Pro Asp Lys Glu Arg Lys
            330                 335                 340

Met Ile Thr Ile Arg Gly Ser Val His Gln Asn Phe Ala Asp Phe Thr
            345                 350                 355

Phe Ala Thr Gly Lys Ile Ile Gly His Met Leu Lys Leu Lys Gly Asp
            360                 365                 370

Ile Asp Ser Asn Ala Ala Ile Asp Leu Ser Asn Lys Ala Ser Leu Ala
375                 380                 385                 390

Phe Leu Gln Lys His Leu Gly Leu His Lys Asp Phe Asp Gln Trp Asp
            395                 400                 405

Cys Leu Ile Glu Gly Asp Asp Glu Asn Leu Ile Pro Gly Thr Asn Ile
            410                 415                 420

Asn Thr Thr Asn Gln His Ile Met Leu Gln Asn Ser Ser Gly Ile Glu
            425                 430                 435

Lys Tyr Asn
440
```